(12) United States Patent
Tse

(10) Patent No.: US 6,582,465 B2
(45) Date of Patent: Jun. 24, 2003

(54) INTEGRATED RIGID FIXATION ORBITAL EXPANDER

(75) Inventor: David T. Tse, Weston, FL (US)

(73) Assignee: University of Miami, Miami, FL (US)

( * ) Notice: Subject to any disclaimer, the term of this patent is extended or adjusted under 35 U.S.C. 154(b) by 74 days.

(21) Appl. No.: 09/815,331

(22) Filed: Mar. 23, 2001

(65) Prior Publication Data

US 2002/0002402 A1 Jan. 3, 2002

Related U.S. Application Data

(60) Provisional application No. 60/192,509, filed on Mar. 28, 2000.

(51) Int. Cl.$^7$ .............................. A61F 2/16; A61F 2/14
(52) U.S. Cl. ........................ 623/6.64; 623/4.1; 623/905
(58) Field of Search ................. 623/4.1, 6.64, 623/905, FOR 103; 606/5, 192

(56) References Cited

U.S. PATENT DOCUMENTS

| | | | | |
|---|---|---|---|---|
| 2,551,781 A | * | 5/1951 | Yuhas | |
| 3,364,501 A | * | 1/1968 | Stafford | |
| 4,671,255 A | * | 6/1987 | Dubrul et al. | 158/1 R |
| 4,685,447 A | * | 8/1987 | Iversen et al. | 128/1 R |
| 4,902,292 A | * | 2/1990 | Joseph | 623/4 |
| 5,074,878 A | * | 12/1991 | Bark et al. | 623/8 |
| 5,192,315 A | * | 3/1993 | Jacob-LaBarre | 623/4 |
| 5,330,529 A | * | 7/1994 | Cepela | 623/4 |
| 5,752,958 A | * | 5/1998 | Wellisz | 606/69 |
| 6,248,130 B1 | * | 6/2001 | Perry | 623/6.64 |
| 6,419,698 B1 | * | 7/2002 | Finger | 623/6.64 |

* cited by examiner

*Primary Examiner*—Bruce Snow
*Assistant Examiner*—Cheryl Miller
(74) *Attorney, Agent, or Firm*—Nixon & Vanderhye PC

(57) ABSTRACT

An integrated rigid fixation orbital expander has a coupling tunnel, an injection port, and a substantially spherically shaped expansion chamber. The coupling tunnel is configured with opposing side walls, a top wall and a bottom wall. The top wall of the coupling tunnel may have a depression denoting a mid-point of the coupling tunnel and serves as an entry point to introduce a needle for injection. The depression lines up with a hole on the vertical arm of a plate. The plate may glide within the coupling tunnel to align the depression with a desired hole in the plate. The injection port has a floor and a dome and a plurality of channels. The floor of the injection port may have a backstop plate to block a needle from further penetration. The dome of the injection port is connected to the bottom wall of the coupling tunnel.

24 Claims, 4 Drawing Sheets

INTEGRATED RIGID FIXATION ORBITAL EXPANDER

CROSS-REFERENCE TO RELATED APPLICATION

This application claims the benefit of U.S. Provisional Application Ser. No. 60/192,509, filed Mar. 28, 2000, the disclosure of which, including the specification, drawings and abstract, is incorporated herein by reference in its entirety.

BACKGROUND OF THE INVENTION

1. Field of the Invention

The present invention relates generally to an orbital implant and, more particularly, to an integrated rigid fixation orbital expander to reduce deformation of the eye socket attributed to anophthalmos or microphthalmos.

2. Description of Related Art

The management of congenital anophthalmos or microphthalmos and early-acquired anophthalmos can be a challenge. Microphthalmos is a congenital or developmental anomaly in which the eyeballs are abnormally small, and occurs with a frequency of 0.22/1000 live births. Anophthalmos is a congenital defect in which an eye never developed in the socket. Both of these abnormalities present minified eyelids with abbreviated palpebral and bulbar conjunctivae. More critically, these two conditions are associated with ipsilateral hypoplasia of the bony orbit.

It is well recognized that orbital volume growth parallels ocular growth, and that the absence of an eye or reduced size of an eye will result in noticeable hemifacial deformity. Recent studies have demonstrated the efficacy of expandable orbital implants to stimulate bone growth and socket enlargement in the anophthalmic orbit. Pressure was found to be an effective stimulant for enlargement of the craniofacial skeleton.

However, insertion of currently available orbital tissue expanders is quite time-consuming and technically difficult in an infant. Furthermore, controlling the direction of expansion and maintaining rigid fixation of the implant in the orbit for uniformed expansion remain problematic. Frequently, the expander protrudes forward or even extrudes during the inflation process, displacing the conformer or breaking open the conjunctiva.

Accordingly, there is a need to address this problem.

SUMMARY OF THE INVENTION

Therefore, one aspect of the present invention is to provide an integrated rigid fixation orbital expander that can overcome the problems of the prior art.

It is another aspect of the invention to provide improved elements and arrangements of an integrated rigid fixation orbital expander for the purposes described which is inexpensive, dependable, and fully effective in accomplishing its intended purposes.

The integrated rigid fixation orbital expander according to one aspect of the invention includes a coupling tunnel, an injection port, and a substantially spherically shaped expansion chamber. The coupling tunnel is configured with opposing side walls, a top wall and a bottom wall. The opposing side walls are dimensioned with desired predetermined heights and the top and bottom walls are dimensioned with desired predetermined widths to conform with the thickness and width, respectively, of a plate that is used to prevent the expander from protruding forward, or out of socket during the inflation process, thus permitting controlled and uniformed expansion. Such a plate may be a plate having a vertical arm and a horizontal arm and a plurality of holes passing therethrough. The coupling tunnel accommodates the vertical arm of such a plate and holds the expander in a centrally located position during the inflation process. The horizontal arm or crossbar of the plate is fixed to the bony rim with screws. The plate may be a rigid and light material, e.g., titanium or the like.

The top wall of the coupling tunnel may have a depression denoting a mid-point of the coupling tunnel and serves as an entry point to introduce a needle for injection. The depression lines up with a hole on the vertical arm of the plate. The plate may glide within the coupling tunnel to align the depression with a desired hole in the plate. This alignment ensures that an injection needle is pointed perpendicular to the integrated rigid fixation orbital expander to gain entrance into the injection port.

The injection port may be housed within the expansion chamber. The injection port has a floor and a dome and a plurality of channels. The floor of the injection port may have a backstop plate to block a needle from further penetration, thereby avoiding inadvertent perforation of the integrated rigid fixation orbital expander. Once an insertion needle hits the backstop plate, injection of saline solution to inflate the integrated rigid fixation orbital expander may commence. The saline solution exits the injection port through the plurality of channels to fill the expander chamber. (The dome of the injection port is connected to the bottom wall of the coupling tunnel.)

The expansion chamber has a pre-inflation state and a post-inflation state corresponding to desired predetermined pre-inflation and post-inflation diameters, respectfully. The expansion chamber accommodates a volume of fluid required to inflate the expander to desired post-inflation state. Once the predetermined post-inflation state of the expander is reached, the expander remains in position until osseous growth equalizes the volume of the uninvolved orbit.

These and other aspects of the present invention will be described in or readily apparent upon further review of the following specification and drawings.

BRIEF DESCRIPTION OF THE DRAWINGS

Preferred embodiments of the invention will be described in relation to the appended drawings, in which.

Similar reference characters denote corresponding features consistently throughout the attached drawings.

DETAILED DESCRIPTION OF PREFERRED EMBODIMENTS

The present invention is an integrated rigid fixation orbital expander to reduce deformation of the eye socket attributed to anophthalmos or microphthalmos.

Figure 1:
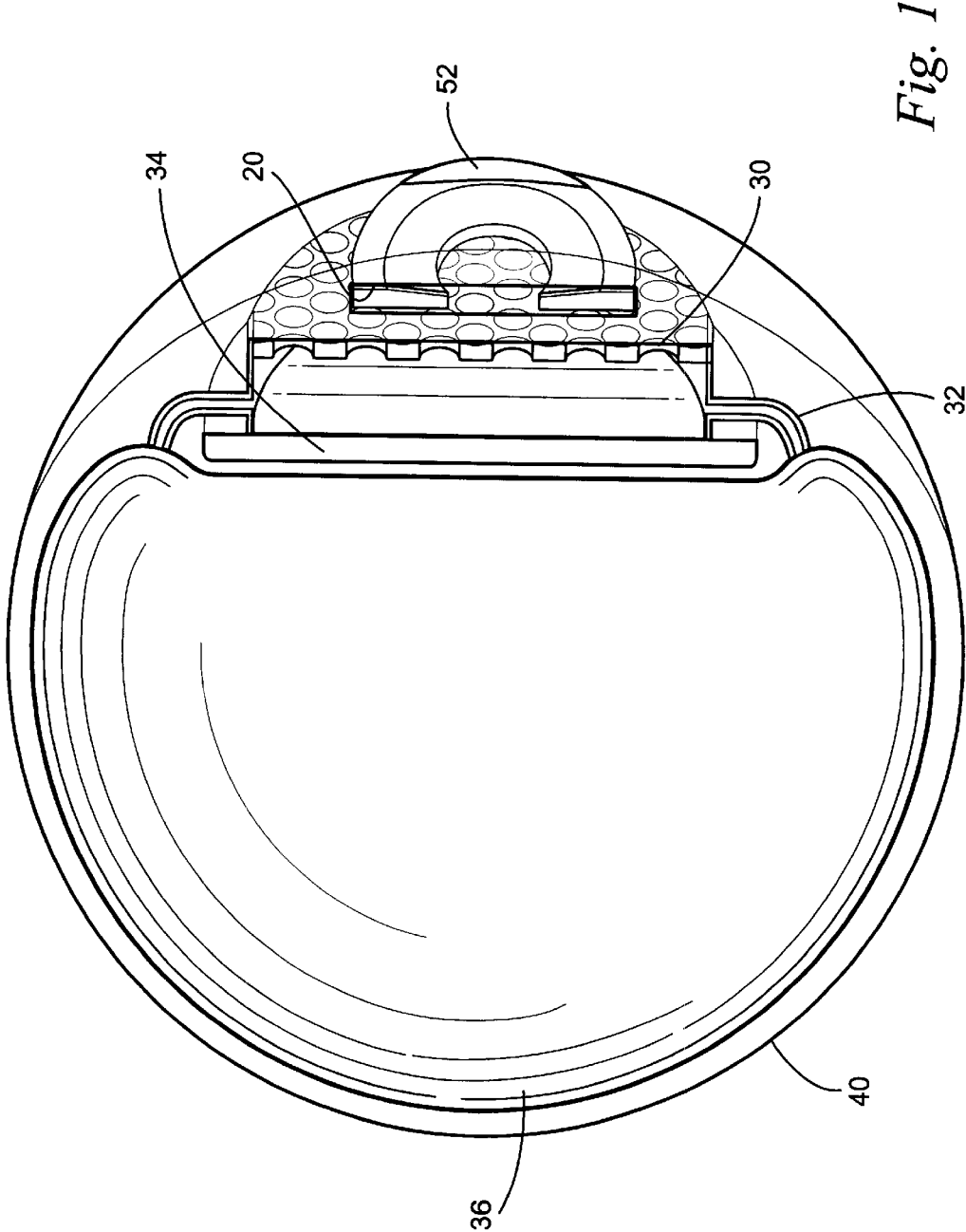
FIG. 1 is a sectional view of an integrated rigid fixation orbital expander according to the present invention.
Figure 2:
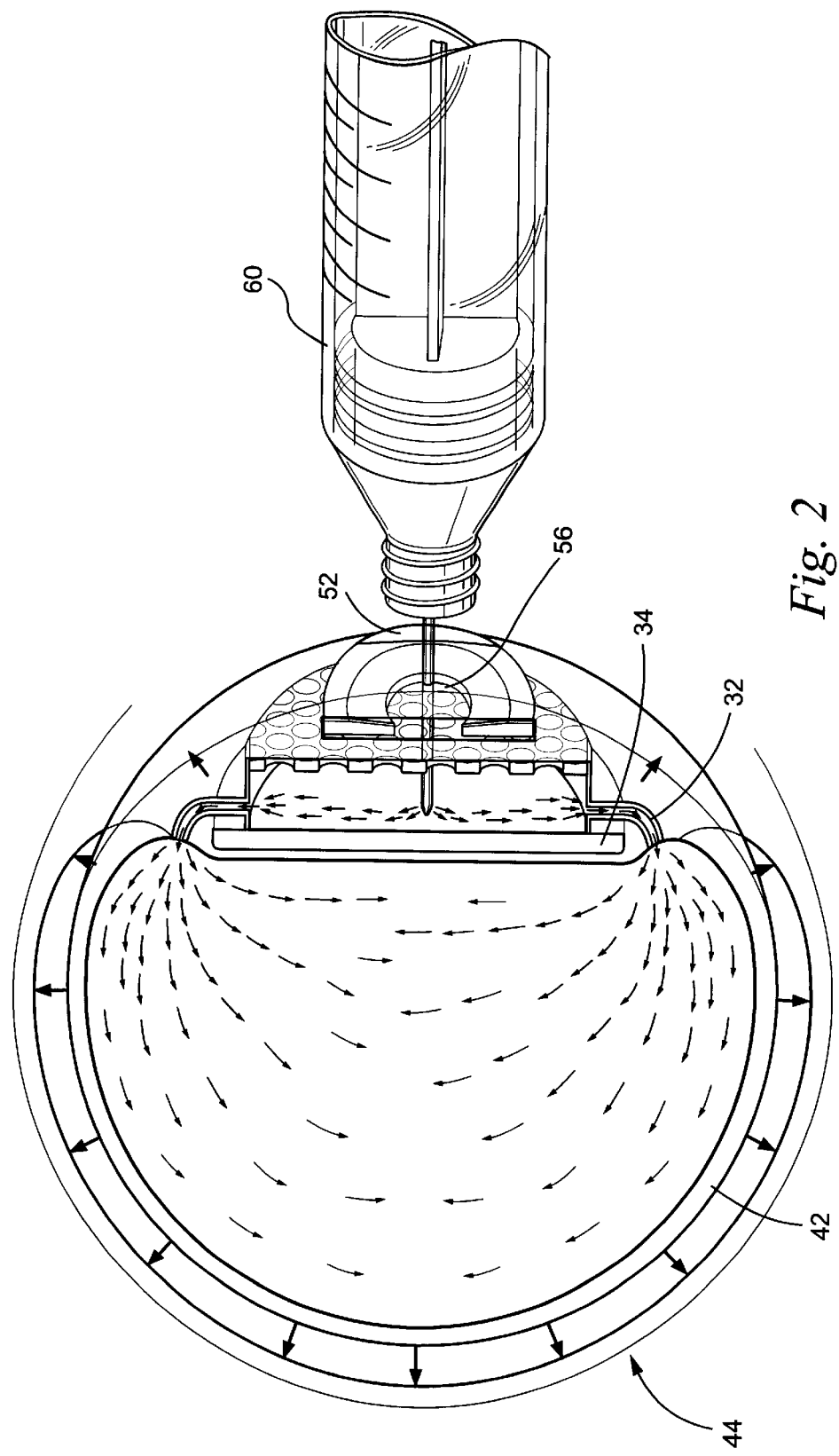
FIG. 2 is a sectional view of an integrated rigid fixation orbital expander in a pre-expansion and a post-expansion condition according to the present invention.
Figure 3:
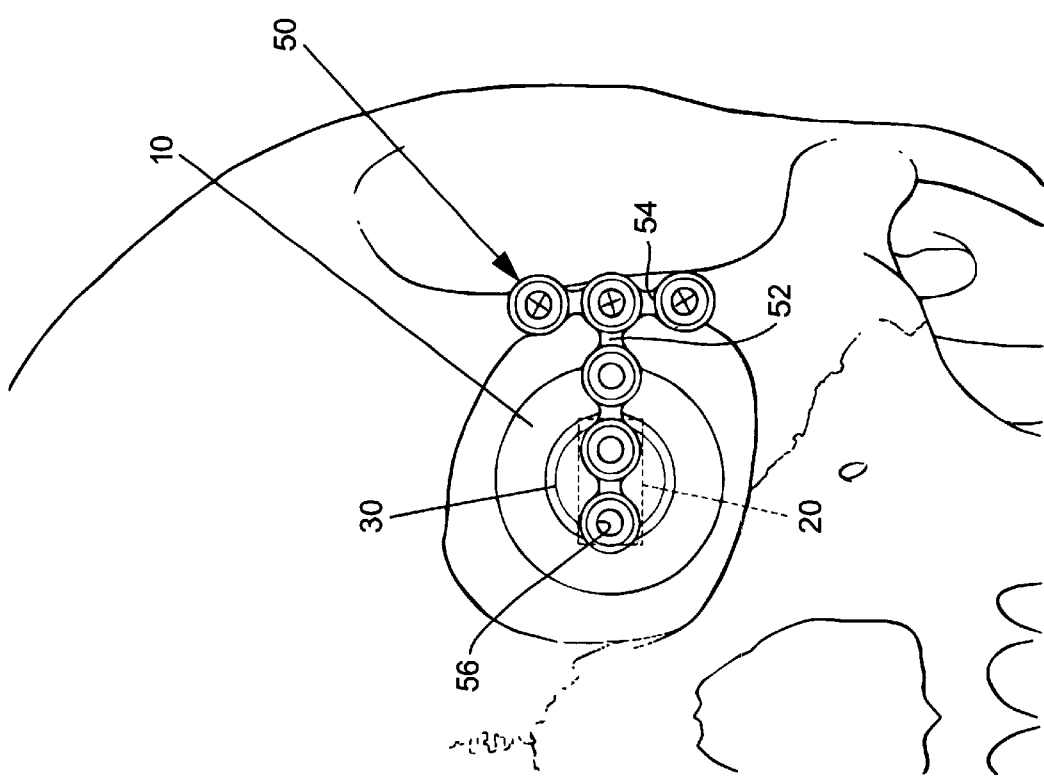
FIG. 3 is a frontal view of an integrated rigid fixation orbital expander according to the present invention in place in an eye socket.
Figure 4:
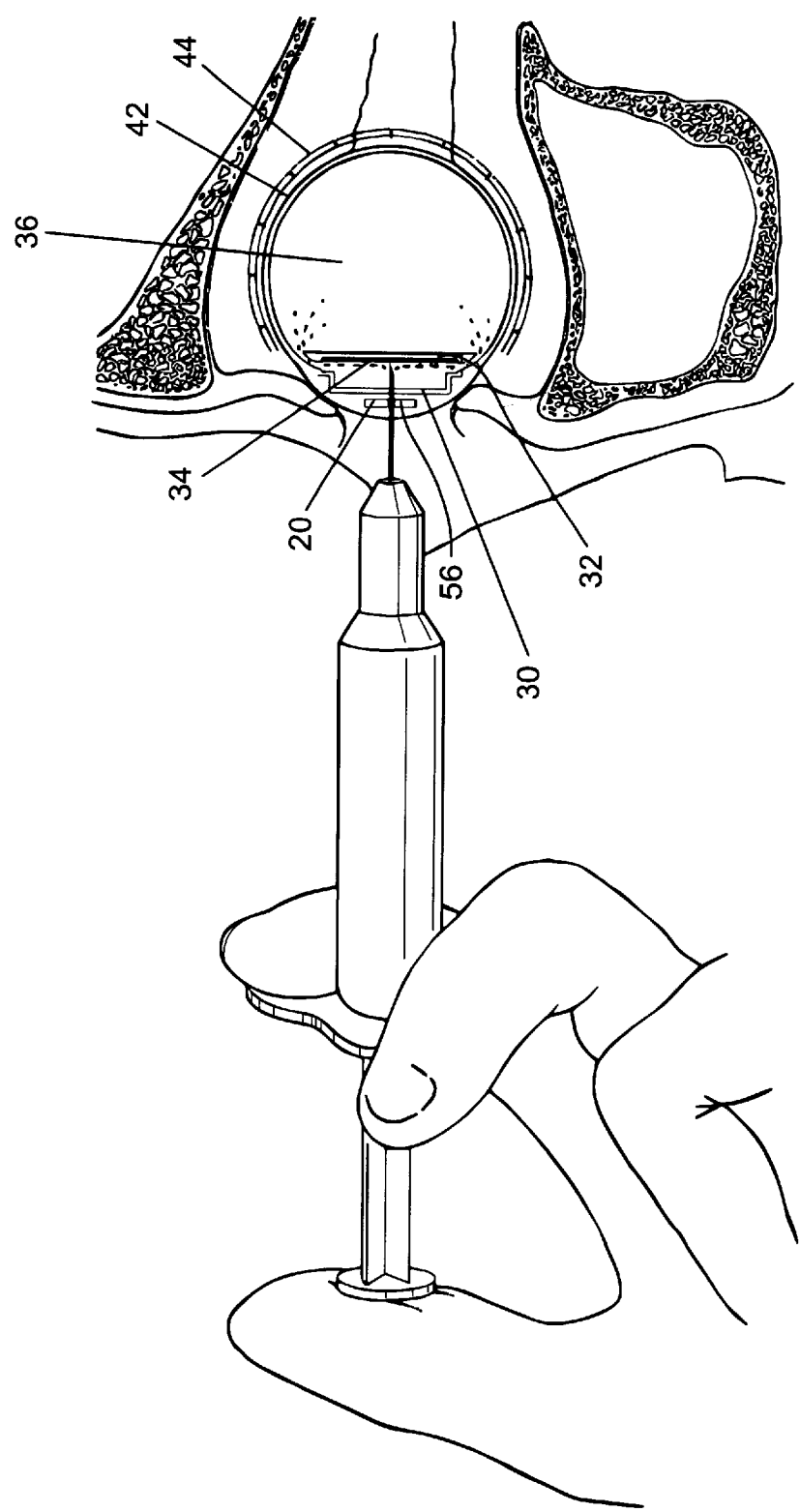
FIG. 4 is a sectional view of an integrated rigid fixation orbital expander according to the present invention in place in an eye socket being injected with a needle.

The integrated rigid fixation orbital expander 10 according to one aspect of the invention is shown in FIGS. 1–4. As shown in FIG. 1, the integrated rigid fixation orbital expander 10 has a coupling tunnel 20, an injection port 30, and a substantially spherically shaped expansion chamber 40. The coupling tunnel 20 is configured with opposing side walls, a top wall and a bottom wall. The opposing side walls are dimensioned with desired predetermined heights and the top and bottom walls are dimensioned with desired predetermined widths to conform with the thickness and width, respectively, of a positioning plate 50 that is used to prevent the expander from protruding forward, or out of socket during the inflation process, thus permitting controlled and uniformed expansion. Such a plate 50 may be a plate having a vertical arm 52 and a horizontal arm 54 and a plurality of holes 56 passing therethrough, as shown in FIG. 3, e.g., a 6-hole T-shaped plate, a 7-hole T-shaped plate, a 10-hole T-shaped plate, a 9-hole L-shaped plate, or the like. The coupling tunnel accommodates the vertical arm 52 of such a plate 50 and holds the expander in a centrally located position during the inflation process. The horizontal arm 54 or crossbar of the plate 50 is fixated to the bony rim with screws. The plate 50 may be a rigid and light material, e.g., titanium or the like.

The top wall of the coupling tunnel 20 may have a depression denoting a mid-point of the coupling tunnel 20 and serves as an entry point to introduce a needle 60 for injection. The depression lines up with a hole 56 on the vertical arm 52 of the plate 50. The plate 50 may glide within the coupling tunnel 20 to align the depression with a desired hole 56 in the plate 50. This alignment ensures that an injection needle 60 is pointed perpendicular to the integrated rigid fixation orbital expander 10 to gain entrance into the injection port 30. The coupling tunnel 20 may be configured out of any known biocompatible material, such as silicon, polyurethane, or the like.

The injection port 30 may be housed within the expansion chamber 40. The Injection port 30 has a floor and a dome and a plurality of channels 32. The floor of the injection port 30 may have a backstop plate 34 to block a needle from further penetration, thereby avoiding inadvertent perforation of the integrated rigid fixation orbital expander 10. The backstop plate 34 may be formed of strong material, such as metal or the like. Preferably, the backstop plate material will not interfere with postoperative magnetic resonance imaging. Once an insertion needle 60 hits the backstop plate 34, injection of saline solution to inflate the integrated rigid fixation orbital expander 10 may commence. The saline solution exits the injection port 30 through the plurality of channels 32 to fill the reservoir 36 of the expander chamber 40. The dome of the injection port 30 is connected to the bottom wall of the coupling tunnel 20, e.g., by fusing or the like, and may be formed of self-sealing material capable of withstanding multiple needle punctures.

The expansion chamber 40 has a pre-inflation state 42 and a post-inflation state 44 corresponding to desired predetermined pre-inflation and post-inflation diameters, respectfully. The expansion chamber 40 accommodates a volume of fluid required to inflate the integrated rigid fixation orbital expander 10 to a desired post-inflation state. The predetermined pre-inflation diameter may be about 14 millimeters and the post-inflation diameter may be about 22 millimeters. The expansion chamber 40 may configured out of any known biocompatible material, such as silicon, polyurethane, or the like. During the serial inflation process, the expander may slide along the articulating vertical arm of the T-plate to assume an optimal position for expansion.

Once the predetermined post-inflation state of the integrated rigid fixation orbital expander 10 is reached, the integrated rigid fixation orbital expander 10 remains in position until osseous growth equalizes the volume of the uninvolved orbit. The integrated rigid fixation orbital expander 10 is then removed and replaced with a conventional orbital implant.

To understand the advantages of the integrated rigid fixation orbital expander 10, a brief description of the cumbersome surgical technique of inserting a conventionally available expander is now described. A conventional orbital expander placement begins with a lateral canthotomy incision. The temporalis fascia is detached from the zygoma and the temporalis muscle separated from the lateral orbital wall. A 3-mm osteotomy is created with a drill at the zygomaticosphenoid suture to allow the inflation tubing to pass from the orbit.

A vertical incision is placed in the temporoparietal scalp, approximately 5 cm above the ear to gain access to the posterior margin of the temporalis muscle. The temporalis fascia is incised and a submuscular tunnel is created between the scalp incision and the lateral orbit for subsequent passage of the inflation tubing. A transverse conjunctival incision is made to access the central orbit and to form a pocket to accommodate the expander. A silk ligature is secured to the inflation tubing on the expander and positioned within the muscle cone. The suture and the attached tubing are guided by a hemostat to the lateral osteotomy drill hole.

The expander's position within the muscle cone is adjusted by exerting tension on the tubing at the lateral orbit. A hemostat is passed through the subtemporalis tunnel to the lateral orbit to grasp the inflation tubing and advance it to the scalp incision. The tubing is then connected to the injection port and secured with a silk ligature. The injection port is positioned within a subcutaneous pocket created behind the scalp incision, and the skin incision is closed in layers.

Insertion of the integrated rigid fixation orbital expander 10 begins with a lateral canthotomy incision to expose the lateral orbital rim. The incision is extended medially across the conjunctiva to fully expose the central orbit. The integrated rigid fixation orbital expander 10 is inserted within the muscle cone and coupled to a multi-hole plate 50, such as a T-shaped, multi-hole micro titanium plate. The vertical arm 52 of the T-shaped plate 50 is inserted into the coupling tunnel 20 on the anterior surface of the integrated rigid fixation orbital expander 10. The vertical arm 52 can slide across the coupling tunnel 20 to adjust for the optimal position for integrated rigid fixation orbital expander placement within the orbit.

Once the optimal position for the integrated rigid fixation orbital expander 10 is determined, the horizontal arm 54 of the T-shaped plate 50 is bent to conform to the curvature of the lateral orbital rim. The composite unit, with the integrated rigid fixation orbital expander 10 coupled to the T-shaped plate 50, is then fixed to the lateral orbital rim with three screws. The cantilevered arm 54 of the T-shaped plate holds the orbital expander 10 in position during the expansion process. The conjunctival and lateral canthotomy incisions are closed to cover the implant. The horizontal arm or crossbar of the plate is fixated to the bony rim with screws.

The inventive orbital expander offers the following advantages over currently available orbital expanders: (1) avoids a lengthy insertion procedure; (2) avoids a scalp incision to form a pocket and tunnel to accommodate an injection port; (3) eliminates the lateral orbital wall osteotomy necessary for injection port connection to the orbital expander, thus permitting a more rapid postoperative recovery; (4) avoids the unpredictable movement of the expander during the inflation process since the implant is indirectly fixed to the orbital rim by a titanium plate; (5) since the titanium plate holds the expander in a fixed central position, sustained and uniform omnidirectional pressure is delivered to constituent bones of the orbit; (6) implant extrusion or displacement of the conformer is unlikely as the inventive orbital expander is coupled to the rigid titanium plate anchored to the bony rim; and (7) avoids disfigurement by eliminating the bulging effect of the injection port on the scalp.

The inventive orbital expander eliminates the need to connect the orbital expander to an injection port located outside of the orbit. Since the inventive orbital expander is anchored into position by coupling it to a titanium plate fixed to the lateral orbital rim, the direction of expansion is controlled and predictable. As the injection port is housed within the new implant, the normally bulging injection port under the skin on the parietal region will no longer be present, thus eliminating this cosmesis problem and permitting an individual to sleep on the side of the head without pressing against the injection port. Another advantage is the ease of insertion of this implant, employing the standard method of intraconal implant placement familiar to surgeons who routinely perform enucleation.

Oculoplastic surgeons and cleft palate-craniofacial reconstructive surgeons will use this self-contained orbital expander for the two conditions described above.

It is to be understood that the present invention is not limited to the preferred embodiments, which are illustrative. Various modifications will occur to those of ordinary skill in the art which are within the scope of the present invention.

What is claimed is:

1. An orbital expander assembly comprising:
   an orbital expander having a substantially spherically shaped expansion chamber, an injection port fluidly coupled to said expansion chamber and through which fluid is selectively added to said expansion chamber whereby the expansion chamber can be inflated; and
   a coupling tunnel having an open end for selectively receiving a positioning plate to position said orbital expander with respect to an eye orbit.

2. The orbital expander assembly according to claim 1, wherein said coupling tunnel is configured with opposing side walls, a top wall and a bottom wall.

3. The orbital expander assembly according to claim 2, wherein said injection port comprises a floor, a dome and a plurality of channels.

4. The orbital expander assembly according to claim 3, wherein said floor comprises a backstop plate.

5. The orbital expander assembly according to claim 4, wherein said dome of said injection port is connected to said bottom wall of said coupling tunnel.

6. The orbital expander assembly according to claim 5, wherein said dome of said injection port is fused to said bottom wall of said coupling tunnel.

7. The orbital expander assembly according to claim 5, wherein said dome of said injection port is formed of self-sealing material capable of withstanding multiple needle punctures.

8. An orbital expander assembly according to claim 2, wherein said opposing side walls of said coupling tunnel are dimensioned with desired predetermined heights and said top and bottom walls are dimensioned with desired predetermined widths.

9. The orbital expander assembly according to claim 2, further comprising a positioning plate having a vertical arm sized and configured for selective insertion in said coupling tunnel and a horizontal arm and a plurality of holes defined therethrough.

10. The orbital expander assembly according to claim 9, wherein said top wall of said coupling tunnel comprises a depression denoting a mid-point of said coupling tunnel and serves as an entry point to introduce a needle for injection.

11. The orbital expander assembly according to claim 9, wherein said positioning plate is titanium.

12. The orbital expander assembly according to claim 11, wherein said depression lines up with a hole on said vertical arm of said plate.

13. The orbital expander assembly according to claim 12, wherein said positioning plate is slidable within said coupling tunnel to align said depression with one of said holes in said plate.

14. The orbital expander assembly according to claim 13, wherein after inflation, the orbital expander may slide relative to the positioning plate disposed in the coupling tunnel to assume an optimal position to exert expansion force.

15. The orbital expander assembly according to claim 1, wherein said injection port is housed within said expansion chamber.

16. The orbital expander assembly according to claim 1, wherein said injection port comprises a floor, a dome and a plurality of channels.

17. The orbital expander assembly according to claim 16, wherein said floor comprises a backstop plate.

18. The orbital expander assembly according to claim 17, wherein said backstop plate is metal.

19. The orbital expander assembly according to claim 16, wherein said dome of said injection port is formed of self-sealing material capable of withstanding multiple needle punctures.

20. The orbital expander assembly according to claim 1, wherein said expansion chamber has a pre-inflation state and a post-inflation state corresponding to predetermined pre-inflation and post-inflation diameters, respectfully.

21. The orbital expander assembly according to claim 20, wherein said predetermined post-inflation diameter is about 22 millimeters.

22. The orbital expander assembly according to claim 1, wherein said expansion chamber is configured out of a biocompatible material.

23. The orbital expander assembly according to claim 22, wherein said expansion chamber is configured out of silicon.

24. The orbital expander assembly according to claim 22, wherein said expansion chamber is configured out of polyurethane.

* * * * *